United States Patent [19]
Miller et al.

[11] Patent Number: 6,160,011
[45] Date of Patent: Dec. 12, 2000

[54] NON-STEROIDAL AGONIST COMPOUNDS AND THEIR USE IN MALE HORMONE THERAPY

[75] Inventors: Duane D. Miller, Germantown; Leonid I. Kirkovsky, Memphis; James T. Dalton, Memphis; Arnab Mukherjee, Memphis, all of Tenn.

[73] Assignee: The University of Tennessee Research Corporation, Knoxville, Tenn.

[21] Appl. No.: 09/086,699

[22] Filed: May 29, 1998

Related U.S. Application Data

[60] Provisional application No. 60/048,299, May 30, 1997.

[51] Int. Cl.⁷ .................................................. A61K 31/275
[52] U.S. Cl. ........................ 514/522; 514/524; 514/616; 514/628
[58] Field of Search ..................... 564/154, 202; 558/417; 514/616, 628, 522, 524

[56] References Cited

U.S. PATENT DOCUMENTS

| | | |
|---|---|---|
| 3,875,229 | 4/1975 | Gold . |
| 4,139,638 | 2/1979 | Neri et al. . |
| 4,191,775 | 3/1980 | Glen . |
| 4,239,776 | 12/1980 | Glen et al. . |
| 4,282,218 | 8/1981 | Glen et al. . |
| 4,386,080 | 5/1983 | Crossley et al. . |
| 4,636,505 | 1/1987 | Tucker . |
| 4,880,839 | 11/1989 | Tucker . |

FOREIGN PATENT DOCUMENTS

| | | |
|---|---|---|
| 0002892 A1 | 7/1979 | European Pat. Off. . |
| 0040932 | 12/1981 | European Pat. Off. . |
| 0100172 A1 | 2/1984 | European Pat. Off. . |
| 52-128329 | 10/1977 | Japan . |
| 54-63047 | 5/1979 | Japan . |
| 1360001 | 7/1974 | United Kingdom . |
| WO 95/19770 | 7/1995 | WIPO . |

OTHER PUBLICATIONS

McKillop et al., "Enantioselective Metabolism and Pharmacokinetics of Casodex in the Male Rat," *Xenobiotica*, 25(6):623–634 (1995).

Tucker et al., "Resolution of the Nonsteriodal Antiandrogen 4'–Cyano–3–[4–fluorophenyl) sulfonyl]–2–hydroxy–2–mehtyl–3'–(trifluoromethyl)–propionanilide and the Determination of the Absolute Configuration of the Active Enantiomer," *J. Med. Chem.*, 31(4):885–887 (1988).

Kirkovsky et al., "Approaches to Irreversible Non–Steroidal Chiral Antiandrogens," 47th Southeast/51st Southwest Joint Regional Meeting of the American Chemical Society, Memphis, TN (Nov. 29–Dec. 1, 1995).

*Primary Examiner*—Shailendra Kumar
*Attorney, Agent, or Firm*—Eitan, Pearl, Latzer & Cohen-Zedek; Mark S. Cohen

[57] ABSTRACT

The present invention relates to a nonsteroidal agonist compound having the formula:

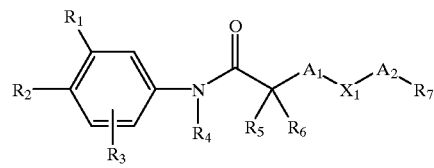

where $R_1$, $R_2$, and $R_3$ are the same or different and are a hydrogen, a nitro, a cyano, a carbamoyl, a halogen, a perfluoroalkyl, a haloalkylamido, an isothiocyanate, an azide, a diazocarbonyl, a substituted oxirane, or a β-chloroethylamine; $R_4$ is a hydrogen, an alkyl, or is joined to $R_5$; $R_5$ is a hydrogen, a hydroxy, an alkoxy, an acyloxy, an amino, an alkylamino, a halogen, an alkyl, a haloalkyl, or is joined to $R_4$; $R_6$ is a hydrogen, an alkyl, or a haloalkyl; $A_1$ and $A_2$ is the same or different, each is direct link or an alkylene; $X_1$ is an oxygen, a sulfur, a sulphinyl, a sulphonyl, an amino, an alkylimino, or an alkylene; $R_7$ is a hydrogen, a halogen, an alkoxy, a haloalkoxy, an acyloxy, a haloacyloxy, an aryloxy, a thioalkyl, a thioraryl, an amino, an alkylimino, an alkylamido group, a haloalkylamido group, or a phenyl optionally substituted with a halogen, a nitro group, an alkyl, a haloalkyl, a cyano, a hydroxyl, a carboxylic group, an amino, an alkylamino group, a dialkylamino group, a bisalkylamino group, a haloalkylamino group, a dihaloalkylamino group, a bishaloalkylamino group, an acylamido group, a diacylamido group, an alkylacylamido group, a haloacylamido group, a bis(haloacyl) imido group, or an alkylhaloacylamido group. The present invention further relates to a method of producing the non-steroidal agonist compound, a composition containing the non-steroidal agonist compound, and methods of binding an androgen receptor, suppressing spermatogenesis, and providing hormonal therapy for androgen-dependent conditions.

9 Claims, No Drawings

NON-STEROIDAL AGONIST COMPOUNDS AND THEIR USE IN MALE HORMONE THERAPY

This application claims the benefit of U.S. Provisional Patent Application Ser. No. 60/048,299, filed May 30, 1997, which is hereby incorporated by reference. This work was funded by grant number R15 HD-35329 from the National Institute of Child Health and Human Development and from the Harriet S. Van Vleet Professorship in Pharmacy to D.D.M. The U.S. Government may have certain rights in the invention.

FIELD OF THE INVENTION

The present invention relates to non-steroidal agonist compounds and their use in male hormone therapy. More particularly, the present invention relates to a non-steroidal agonist for the androgen receptor and its use in male hormone therapy.

BACKGROUND OF THE INVENTION

The androgen receptor ("AR") is a ligand-activated transcriptional regulatory protein that mediates induction of male sexual development and function through its activity with endogenous androgens. Androgens are generally known as the male sex hormones. The androgenic hormones are steroids which are produced in the body by the testis and the cortex of the adrenal gland, or synthesized in the laboratory. Androgenic steroids play an important role in many physiologic processes, including the development and maintenance of male sexual characteristics such as muscle and bone mass, prostate growth, spermatogenesis, and the male hair pattern (Matsumoto, *Endocrinol. Met. Clin. N. Am.* 23:857-75 (1994)). The endogenous steroidal androgens include testosterone and dihydrotestosterone ("DHT"). Testosterone is the principal steroid secreted by the testes and is the primary circulating androgen found in the plasma of males. Testosterone is converted to DHT by the enzyme 5a-reductase in many peripheral tissues. DHT is thus thought to serve as the intracellular mediator for most androgen actions (Zhou, et al., *Molec. Endocrinol.* 9:208-18 (1995)). Other steroidal androgens include esters of testosterone, such as the cypionate, propionate, phenylpropionate, cyclopentylpropionate, isocarporate, enanthate, and decanoate esters, and other synthetic androgens such as 7-Methyl-Nortestosterone ("MENT") and its acetate ester (Sundaram et al., "7 Alpha-Methyl-Nortestosterone(MENT): The Optimal Androgen For Male Contraception," *Ann. Med.*, 25:199–205 (1993) ("Sundaram")).

Because the AR is involved in male sexual development and function, the AR is a likely target for effecting male contraception or other forms of hormone replacement therapy.

Worldwide population growth and social awareness of family planning have stimulated a great deal of research in contraception. Contraception is a difficult subject under any circumstance. It is fraught with cultural and social stigma, religious implications, and, most certainly, significant health concerns. This situation is only exacerbated when the subject focuses on male contraception. Despite the availability of suitable contraceptive devices, historically, society has looked to women to be responsible for contraceptive decisions and their consequences. Although health concerns over sexually transmitted diseases has made men more aware of the need to develop safe and responsible sexual habits, women still often bear the brunt of contraceptive choice. Women have a number of choices from temporary mechanical devices such as sponges and diaphragms to temporary chemical devices such as spermicides. Women also have at their disposal more permanent options such as physical devices like IUDs and cervical caps as well as more permanent chemical treatments such as birth control pills and subcutaneous implants.

However, to date, the only options available for men include the use of condoms and a vasectomy. Condom use, however is not favored by many men because of the reduced sexual sensitivity, the interruption in sexual spontaneity, and the significant possibility of pregnancy caused by breakage or misuse. Vasectomies are also not favored. If more convenient methods of birth control were available to men, particularly long term methods which required no preparative activity immediately prior to a sexual act, such methods could significantly increase the likelihood that men would take more responsibility for contraception.

Despite prolonged research, spermatogenesis remains a poorly understood physiologic process. A number of strategies to interfere with normal hormonal control of spermatogenesis have been employed, including androgens, prostagens, and luteinizing hormone releasing hormone ("LHRH") analogs (Wu, "Male Contraception: Current Status and Future Prospects," *Clin. Endocrin.* 29:443:65 (1988) ("Wu 1988")). Administration of the male sex steroids (e.g., testosterone and its derivatives) has shown particular promise in this regard due to the combined gonadotropin-suppressing and androgen-substituting properties of these compounds (Steinberger et al., "Effect of Chronic Administration of Testosterone Enanthate on Sperm Production and Plasma Testosterone, Follicle Stimulating Hormone, and Luteinizing Hormone Levels: A Preliminary Evaluation of a Possible Male Contraceptive," *Fertility and Sterility* 28:1320-28 (1977)). Chronic administration of high doses of testosterone completely abolishes sperm production (azoospermia) or reduces it to a very low level (oligospermia). The degree of spermatogenic suppression necessary to produce infertility is not precisely known. However, a recent report by the World Health Organization showed that weekly intramuscular injections of testosterone enanthate result in azoospermia or severe oligospermia (i.e., less than 3 million sperm per ml) and infertility in 98% of men receiving therapy (World Health Organization Task Force on Methods for Regulation of Male Fertility, "Contraceptive Efficacy of Testosterone-Induced Azoospermia and Oligospermia in Normal Men," *Fertility and Sterility* 65:821-29 (1996)).

The main disadvantages of steroidal male contraceptives lie in their undesirable physicochemical and pharmacokinetic properties. Testosterone is readily absorbed after oral administration, but demonstrates little androgenic effect due to rapid hepatic metabolism prior to reaching the systemic circulation. Rapid absorption and metabolism also preclude the use of testosterone via intramuscular injection.

A variety of testosterone esters have been developed which are more slowly absorbed after intramuscular injection and, thus, result in greater androgenic effect. Testosterone enanthate is the most widely used of these esters. While testosterone enanthate has been valuable in terms of establishing the feasibility of hormonal agents for male contraception, it has several drawbacks, including the need for weekly injections and the presence of supraphysiologic peak levels of testosterone immediately following intramuscular injection (Wu, "Effects of Testosterone Enanthate in Normal Men: Experience From a Multicenter Contraceptive Efficacy Study," *Fertility and Sterility* 65:626-36 (1996)).

Steroidal ligands which bind the AR and act as androgens (e.g. testosterone enanthate) or as antiandrogens (e.g. cyproterone acetate) have been known for many years and are used clinically (Wu 1988). Although nonsteroidal antiandrogens are in clinical use for hormone-dependent prostate cancer, nonsteroidal androgens have not been reported. For this reason, research on male contraceptives has focused solely on steroidal compounds. However, data obtained during the development of nonsteroidal antiandrogens suggest that nonsteroidal androgens may be realized. In 1988, Tucker et al., ("Synthesis and Structure-Activity Relationships of 3-Substituted Derivatives of 2-Hydroxypropioanilides," *J. Med. Chem.* 31:954-59 (1988) ("Tucker 1988a")), using hydroxyflutamide as a lead compound, synthesized a large series of compounds with systematic structural modifications and tested their AR binding affinity and in vivo antiandrogenic activity. As a result of these studies, many of the structural elements required for nonsteroidal AR binding have been delineated (Tucker 1988a; Glen et al., "Structure-Activity Relationships Among Nonsteroidal Antiandrogens," Proceedings of the Third SCI-RSC Medicinal Chemistry Symposium, Royal Society of Chemistry: London, p. 345-61 (1986) ("Glen")). Glen showed that the AR binding affinity of a series of hydroxyflutamide analogs was dependent on the presence of an electron deficient aromatic ring separated from the tertiary carbinol by an amide link.

Electron-withdrawing groups presented at the 3- and 4- positions of the anilide ring further enhanced the AR binding affinity, particularly when the 4- substituent was cyano or nitro and the 3-substituent was chloro or trifluoromethyl. Physicochemical studies showed that the dominant conformation in these compounds was that in which the amide NH hydrogen bonds to the OH group, as opposed to that in which OH hydrogen bonds to the amidic carbonyl. This alignment between the NH and OH groups confers a planar geometry to the molecule and additional proton-donor ability to the OH group. It is also thought to play a crucial role in AR interaction of these compounds. This effect is also influenced by the electronic properties of other ring substituents (Glen). Tucker (Tucker 1988a; Tucker et al., "Resolution of Nonsteroidal Antiandrogen 4-Cyano-3-[(4-fluorophenyl) sulfonyl)]-2-hydroxy-2-methyl-3'-(trifluoromethyl)-propionanilide and Determination of the Absolute Configuration of the Active Enantiomer," *J. Med. Chem.* 31:885-87 (1988) ("Tucker 1988b")) synthesized and evaluated the in vivo activity of a series of arylthio derivatives, of which Casodex is an example. An infrared study on two representative sulfones showed that the dominant (>95%) conformation in nonpolar solvents is a structure in which the OH group is bound intramolecularly to a sulfonyl group oxygen atom (Morris, et al., "Non-Steroidal Antiandrogens: Design of Novel Compounds Based on an Infrared Study of Dominant Conformation and Hydrogen Bonding Properties of a Series of Anilide Antiandrogens," *J. Med. Chem.* 34:447-55 (1991)). This suggests that the OH group is not free to participate in AR interactions and that a different binding mechanism may be operative for these compounds. However, an NMR study by the same group indicated that the hydrogen bond to the sulfonyl group is disrupted in proton acceptor solvents, such as the aqueous environment of the AR, and enables the OH group to interact as originally proposed (Tucker 1988a). Teutsch et al., "Non-Steroidal Antiandrogens: Synthesis and Biological Profile of High Affinity Ligands for the Androgen Receptor," *J. Steroid Biochem. Molec. Biol.* 48:111-19 (1994) recently reported a series of N-substituted arylthiohydantoin derivatives with AR binding affinities over 100-fold greater than those reported for flutamide, nilutamide, and Casodex. The planar geometry of these compounds corroborates the significance of this conformation with regard to AR interaction with nonsteroidal ligands. Casodex, recently given the generic name bicalutamide, was developed as a result of these studies, and has several advantages over other antiandrogen therapies (Tucker 1988a; Tucker 1988b). Casodex has about 2 to 4 times the AR binding affinity of flutamide and nilutamide, greater in vivo potency, improved tolerance, a long biological half-life (6 days in man) compatible with once daily dosing, and is well absorbed after oral administration (Neri, et al., "Effects of a Novel Non-Steroidal Antiandrogen on Canine Prostatic Hyperplasia," *Invest. Urol.* 10:123-130 (1972); Furr, A Novel Non-Steroidal Peripherally Selective Antiandrogen. In: Management of Advanced Cancer of Prostate and Bladder," New York, A. R. Liss, pp. 13–26 (1988); Kennealey, et al., "Use of the Non-Steroidal Antiandrogen Casodex in Advanced Prostatic Carcinoma," *Urol. Clin. N. Am.* 18(1):99-110 (1991)).

In addition to antiandrogens, these studies uncovered a number of structural analogs demonstrating partial agonist activity. Tucker (1988a) showed that substitution with a trifluoromethyl 3-substituent apparently resulted in partial agonist activity, and that partial agonist activity was enhanced when the 4-substituent was nitro, as opposed to cyano. However, it is important to note that the objective of the Tucker studies was to identify nonsteroidal antiandrogens for treatment of prostate cancer. Although several partial agonists were identified, the structural properties required for androgenic activity were not further investigated. In addition, Tucker measured in vivo functional activity. As such, a compound which produces potent androgenic effects upon interaction with the AR but is rapidly metabolized would demonstrate poor in vivo agonism and, therefore, interfere with the identification of valid structure activity relationships. Thus, the animal model used by Tucker was not designed for and was incapable of identifying compounds with AR agonist activity. Molecular cloning and characterization of the cDNA encoding the AR (Lubahn, et al., "The Human Androgen Receptor: Complementary Deoxyribonucleic Acid Cloning, Sequence Analysis and Gene Expression in Prostate," *Molec. Endocr.* 2:1265-75 (1988); Chang, et al., "Structural Analysis of Complementary DNA and Amino Acid Sequences of Human and Rat Androgen Receptors," *PNAS* 85:7211-15 (1988); Trapman, et al., "Cloning, Structure and Expression of a cDNA Encoding the Human Androgen Receptor," *Biochem. Biophys. Res. Commun.* 153:241-48 (1988)) now permit direct measurement of the functional activity of AR ligands in the absence of potentially confounding pharmacokinetic factors. Also, Tucker utilized racemic mixtures of the compounds of interest for their in vitro and in vivo experiments. This is of particular significance given a recent report regarding the stereoselective pharmacokinetics of Casodex (McKillop, et al., "Metabolism and Enantioselective Pharmacokinetics of Casodex in Man," *Xenobiotica* 23:1241-1253 (1993) ("McKillop")). McKillop showed that the elimination half-life of R-Casodex (4.2 days) was significantly longer than that of the S-enantiomer ($t_{1/2}$, 19 hrs) in healthy male volunteers receiving a single oral dose of the racemic mixture. Further, area under the plasma concentration-time profile (AUC) for the R-enantiomer was 130-fold greater than that of S-Casodex, indicating a significant difference in physiologic exposure to the two isomers. Differences in functional activity reported by Tucker 1988a and 1988b did not account for potential stereoselective differences in drug metabolism.

In summary, many of the structural elements and geometry required for nonsteroidal ligand binding to the AR have been determined. However, a significant knowledge gap exists with regard to nonsteroidal agonists, due to the fact that previous studies focused on elucidation of structure-activity relationships for receptor antagonists and used test systems providing potentially misleading results. Studies utilizing stereochemically pure compounds and more specific measures of functional activity were necessary to elucidate the structure-activity relationship for nonsteroidal agonism.

The present invention is directed toward overcoming these above-noted deficiencies.

SUMMARY OF THE INVENTION

The present invention relates to a non-steroidal agonist compound having the formula:

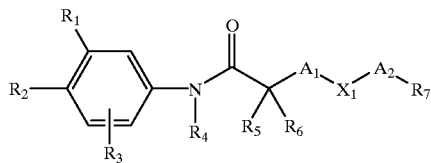

where $R_1$, $R_2$ and $R_3$, are the same or different and are a hydrogen, a nitro, a cyano, a carbamoyl, a halogen, a perfluoroalkyl, a haloalkylamido, an isothiocyanate, an azide, a diazocarbonyl, a substituted oxirane, or a β-chloroethylamine $R_4$ is a hydrogen, an alkyl, or is joined to $R_5$;

$R_5$ is a hydrogen, a hydroxy, an alkoxy, an acyloxy, an amino, an alkylamino, a halogen, an alkyl, a haloalkyl, or is joined to $R_4$;

$R_6$ is a hydrogen, an alkyl, or a haloalkyl;

$A_1$ and $A_2$ are the same or different, and each is a direct link or an alkylene;

$X_1$ is a halogen, an oxygen, a sulfur, a sulphinyl, a sulphonyl, an amino, or an alkylimino, or an alkylene; and $R_7$ is a hydrogen, a halogen, an alkoxy, a haloalkoxy, an acyloxy, a haloacyloxy, an aryloxy, a thioalkyl, a thioaryl, an amino, an alkylimino, an alkylamido group, a haloalkylamido group, or a phenyl optionally substituted with a halogen, a nitro group, an alkyl, a haloalkyl, a cyano, a hydroxyl, a carboxylic group, an amino, an alkylamino group, a dialkylamino group, a bisalkylamino group, a haloalkylamino group, a dihaloalkylamino group, a bishaloalkylamino group, an acylamido group, a diacylamido group, an alkylacylamido group, a haloacylamido group, a bis(haloacyl)imido group, or an alkylhaloacylamido group.

The present invention also relates to a method of binding a compound to a androgen receptor which includes contacting the androgen receptor with a non-steroidal agonist compound under conditions effective to bind the non-steroidal agonist compound to the androgen receptor.

Another aspect of the present invention relates to a method of suppressing spermatogenesis in a male patient which includes contacting an androgen receptor of a male patient with a non-steroidal agonist compound under conditions effective to suppress spermatogenesis.

The present invention also relates to a method of hormone therapy which includes contacting an androgen receptor of a patient with a non-steroidal agonist compound under conditions effective to bind the non-steroidal agonist compound to the androgen receptor and effect a change in an androgen-dependent condition.

The present invention also relates to a pharmaceutical composition which includes a non-steroidal agonist compound of the present invention and a pharmaceutically suitable carrier.

Still another aspect of the present relates to a method of producing a non-steroidal AR agonist compound of the present invention.

The novel non-steroidal AR agonists of the present invention, either alone or as a composition, are useful as a male contraceptive or in the treatment of a variety of hormone-related conditions, such as hypogonadism, sarcopenia, erythropoiesis, and osteoporesis. The non-steroidal AR agonists of the present invention offer a significant advance over steroidal androgen treatment because the non-steroidal AR agonists will not be accompanied by serious side effects, inconvenient modes of administration, or high costs. Moreover, the non-steroidal AR agonists offer several advantages; namely, oral bioavailability, lack of cross-reactivity with other steroid receptors, and long biological half-lives.

DETAILED DESCRIPTION OF THE INVENTION

The present invention relates to a non-steroidal agonist compound having the formula:

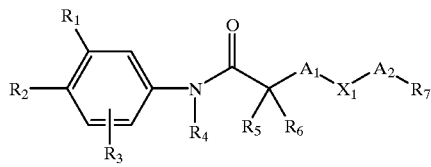

where $R_1$, $R_2$, and $R_3$ are the same or different and are a hydrogen, a nitro, a cyano, a carbamoyl, a halogen, a perfluoroalkyl, a haloallylamido, an isothiocyanate, an azide, a diazocarbonyl, a substituted oxirane, or a β-chloroethylamine;

$R_4$ is a hydrogen, an alkyl, or is joined to $R_5$;

$R_5$ is a hydrogen, a hydroxy, an alkoxy, an acyloxy, an amino, an alkylamino, a halogen, an alkyl, a haloalkyl, or is joined to $R_4$;

$R_6$ is a hydrogen, an alkyl, or a haloalkyl;

$A_1$ and $A_2$ are the same or different, and each is a direct link or an alkylene;

$X_1$ is a halogen an oxygen, a sulfur, a sulphinyl, a sulphonyl, an amino, an alkylimino, or an alkylene;

$R_7$ is a hydrogen, a halogen, an alkoxy, a haloalkoxy, an acyloxy, a haloacyloxy, an aryloxy, a thioalkyl, a thioaryl, an amino, an alkylimino, an alkylamido group, a haloalkylamido group, or a phenyl optionally substituted with a halogen, a nitro group, an alkyl, a haloalkyl, a cyano, a hydroxyl, a carboxylic group, an amino, an alkylamino group, a dialkylamino group, a bisalkylamino group, a haloalkylamino group, a dihaloalkylamino group, a bishaloalkylamino group, an acylamido group, a diacylamido group, an alkylacylamido group, a haloacylamido group, a bis(haloacyl)imido group, or an alkylhaloacylamido group. The compound binds to an androgen receptor.

The subject invention is best understood through a discussion of receptors and signal transduction pathways. Cells in higher animals normally communicate by means of hundreds of kinds of extracellular signaling molecules, including proteins, small peptides, amino acids, nucleotides, steroids, retinoids, fatty acid derivatives, and even dissolved gases such as nitric oxide and carbon monoxide. These signaling molecules relay a "signal" to another cell (i.e., a "target cell"), generally affecting a cellular function. As used herein, receptors for extracellular signaling molecules are collectively referred to as "cell signaling receptors".

Many cell signaling receptors are transmembrane proteins on a cell surface; when they bind an extracellular signaling molecule (i.e., a ligand), they become activated so as to generate a cascade of intracellular signals that alter the behavior of the cell. In contrast, in some cases, the receptors are inside the cell and the signaling ligand has to enter the cell to activate them; these signaling molecules therefore must be sufficiently small and hydrophobic to diffuse across the plasma membrane of the cell. As used herein, these receptors are collectively referred to as "intracellular cell signaling receptors".

Steroid hormones are one example of small hydrophobic molecules that diffuse directly across the plasma membrane of target cells and bind to intracellular cell signaling receptors. These receptors are structurally related and constitute the intracellular receptor superfamily (or steroid-hormone receptor superfamily). Steroid hormone receptors include progesterone receptors, estrogen receptors, androgen receptors, glucocorticoid receptors, and mineralocorticoid receptors. The present invention is particularly directed to androgen receptors.

In addition to ligand binding to the receptors, the receptors can be blocked to prevent ligand binding. When a substance binds to a receptor, the three-dimensional structure of the substance fits into a space created by the three-dimensional structure of the receptor in a ball and socket configuration. The better the ball fits into the socket, the more tightly it is held. This phenomenon is called affinity. If the affinity of a substance is greater than the original hormone, it will compete with the hormone and bind the binding site more frequently. Once bound, signals may be sent through the receptor into the cells, causing the cell to respond in some fashion. This is called activation. On activation, the activated receptor then directly regulates the transcription of specific genes. But the substance and the receptor may have certain attributes, other than affinity, in order to activate the cell. Chemical bonds between atoms of the substance and the atoms of the receptors may form. In some cases, this leads to a change in the configuration of the receptor, which is enough to begin the activation process (called signal transduction). As a result, substances can be made which bind receptors and activate them (called receptor agonists) or inactivate them (called receptor antagonists).

The present invention is directed to compounds which are agonist compounds, and are, therefore, useful in binding to and activating steroidal hormone receptors. The compounds are non-steroidal. Preferably, the agonist compound of the present invention is an agonist which binds the androgen receptor. Preferably, the compound has high affinity for the androgen receptor. The compound may bind either reversibly or irreversibly to the androgen receptor. The compound of the present invention may contain a functional group (affinity label) that allows alkylation of the androgen receptor (i.e. covalent bond formation). Thus, in this case, the compound binds irreversibly to the receptor and, accordingly, cannot be displaced by a steroid, such as the endogenous ligands dihydrotestosterone and testosterone. It is preferable, however, for the compounds of the present invention reversibly to bind the androgen receptor.

Particularly preferred are the non-steroidal agonist compounds below.

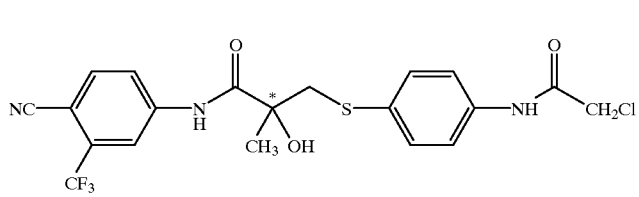

Compound C-1

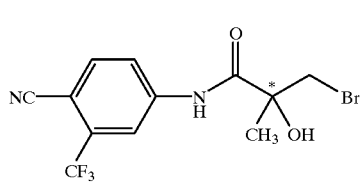

Compound C-2

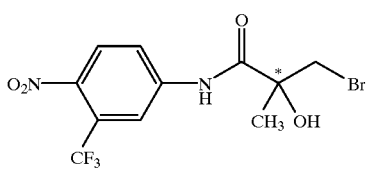

Compound C-3

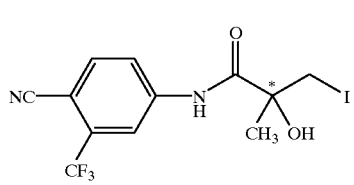

Compound C-4

-continued
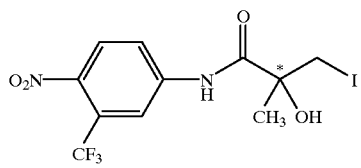
Compound C-5
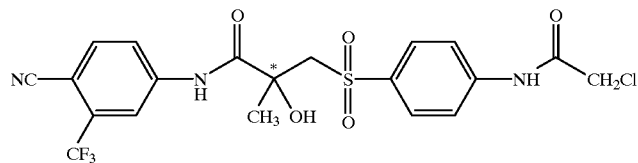
Compound C-6
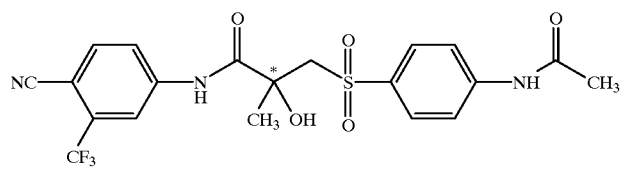
Compound C-7
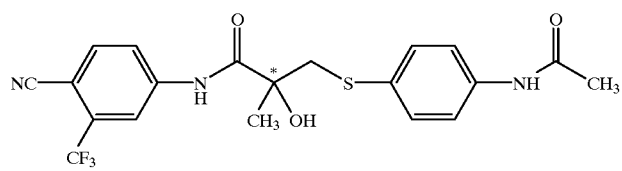
Compound C-8
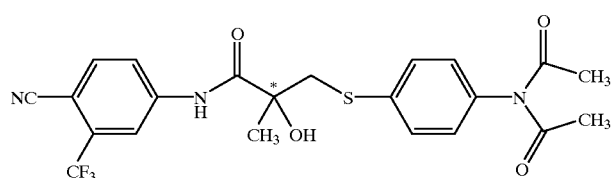
Compound C-9
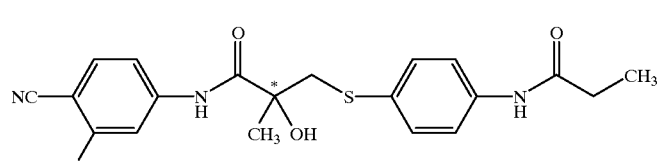
Compound C-10
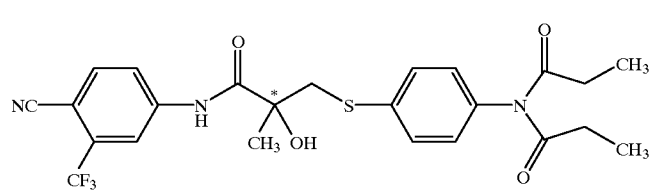
Compound C-11
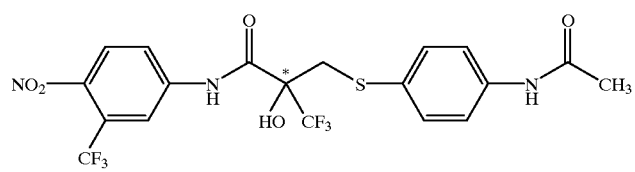
Compound C-12

-continued

Compound C-13

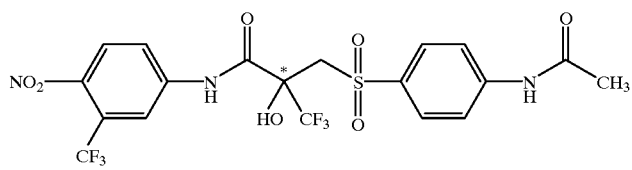

Compound C-14

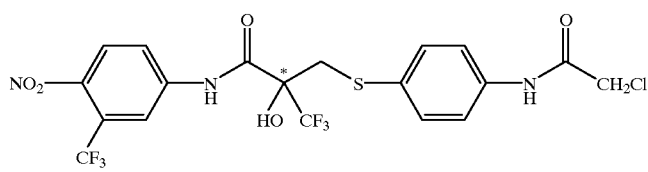

Compound C-15

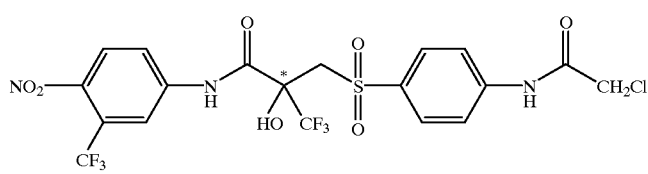

The compounds of the present invention include racemic mixtures of the R and S enantiomers. Preferred are substantially pure R and S enantiomers of the compounds. "Substantially pure" is defined herein as greater than about 95% preponderance of one isomer.

According to one aspect of the present invention, a method is provided for binding the non-steroidal agonist compounds of the present invention to an androgen receptor by contacting the receptor with a non-steroidal agonist compound under conditions effective to cause the non-steroidal agonist compound to bind the androgen receptor. The binding of the non-steroidal agonist compounds to the androgen receptor enables the compounds of the present invention to be useful as a male contraceptive and in a number of hormone therapies. The agonist compounds bind to and activate the androgen receptor. Binding of the agonist compound is either reversible or irreversible, preferably reversible.

According to one aspect of the present invention, a method is provided for suppressing spermatogenesis by contacting an androgen receptor of a patient with a non-steroidal agonist compound under conditions effective to bind the non-steroidal agonist compound to the androgen receptor and suppress spermatogenesis. Although the exact mechanism by which the non-steroidal agonists of the present invention exert their function is not known, without being bound to any particular theory, it is believed that the non-steroidal agonist compounds of the present invention, by binding to androgen receptors, block the activity of the negative feedback pathway for testosterone regulation. In the negative feedback pathway, elevated testosterone levels in the blood normally causes the pituitary gland to decrease production of luteinizing hormone ("LH") and luteinizing hormone-releasing hormone ("LHRH"), which regulates testosterone production as part of the hypothalamic-pituitary-gonadal axis (Burns-Cox and Gingell, "The Andropause: Fact or Fiction?," Postgad. Med. J. 73:553-56 (1997), which is hereby incorporated by reference).

According to another aspect of the present invention, a method is provided for hormonal therapy in a patient (i.e., suffering from an androgen-dependent condition) which includes contacting an androgen receptor of a patient with a non-steroidal agonist compound under conditions effective to bind the non-steroidal agonist compound to the androgen receptor and effect a change in an androgen-dependent condition. Androgen-dependent conditions which may be treated according to the present invention include those conditions which are associated with aging, such as hypogonadism, sarcopenia, erythropoiesis, osteoporosis, and any other conditions later determined to be dependent upon low androgen (e.g., testosterone) levels. Androgen therapies have been shown to have a positive effect on bone density, muscle mass, red blood cell count and hemoglobin levels, and sexual function. See Swerdloff and Wang, "Androgen Deficiency and Aging in Men," West J. Med. 159:579-85 (1993); Tenover, "Testosterone and the Aging Male," J. Andrology 18(2):103-06 (1997); Burns-Cox and Gingell, "The Andropause: Fact or Fiction?," Postgrad. Med. J. 73:553-56 (1997); Tenover, "Androgen Administration to Aging Men," Clin. Andrology 23:877-92 (1994), which are hereby incorporated by reference.

The compounds herein may be made up in any suitable form appropriate for the desired use; e.g., oral, parenteral (for example, subcutaneously, intravenously, intramuscularly, intraperitoneally, by intranasal instillation, or by application to mucous membranes, such as that of the nose, throat, and bronchial tubes, or by instillation into hollow organ walls or newly vascularized blood vessels) or topical administration. Suitable dosage forms for oral use include tablets, dispersible powders, granules, capsules, suspensions, syrups, and elixirs. The compounds may be administered alone or with suitable pharmaceutical diluents or carriers. Inert diluents and carriers for tablets include, for example, calcium carbonate, sodium carbonate, lactose, and talc. Tablets may also contain granulating and disintegrating agents such as starch and alginic acid, binding agents such as starch, gelatin, and acacia, and lubricating agents such as magnesium stearate, stearic acid, and talc. Tablets may be uncoated or may be coated by known techniques to delay disintegration and absorption. Inert diluents and carriers which may be used in capsules include, for example, calcium carbonate, calcium phosphate, and kaolin. Suspensions, syrups, and elixirs may contain conventional excipients, for example, methyl cellulose, tragacanth, sodium alginate; wetting agents, such as lecithin and polyoxyethylene stearate; and preservatives, e.g., ethyl-p-hydroxybenzoate.

Dosage forms suitable for parenteral administration include solutions, suspensions, dispersions, emulsions, and the like. They may also be manufactured in the form of sterile solid compositions which can be dissolved or suspended in sterile injectable medium immediately before use. They may contain suspending or dispersing agents known in the art.

It will be appreciated that the actual preferred amount of the compound to be administered according to the present invention will vary according to the particular compound, the particular composition formulated, and the mode of administration. Many factors that may modify the action of the compound can be taken into account by those skilled in the art; e.g., body weight, diet, time of administration, route of administration, rate of excretion, condition of the subject, drug combinations, and reaction sensitivities and severities. Administration can be carried out continuously or periodically within the maximum tolerated dose. Optimal administration rates for a given set of conditions can be ascertained by those skilled in the art using conventional dosage administration tests.

The acylanilides of the invention may be manufactured by any chemical process known to be suitable for the manufacture of chemically-analogous compounds. Examples of suitable chemical processes for manufacturing acylanilides are shown in U.S. Pat. No. 4,636,505 to Tucker, which is hereby incorporated by reference. One preferred process for the manufacture of an acylanilide of the invention comprises the reaction of an amine of the formula:

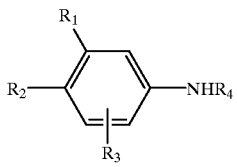

wherein $R_1$, $R_2$, $R_3$, are the same or different, and each is a hydrogen, a nitro, a cyano, a carbamoyl, a halogen, a perfluoroalkyl, a haloalkylamido, an isothiocyanate, an azide, a diazocarbonyl, a substituted oxirane, a β-chloroethylarnine, or other defined and exemplified substituents, and $R_4$ is a hydrogen, or an alky, with an acid of the formula:

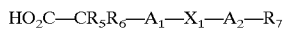

wherein $R_5$ is a hydrogen, a hydroxy, an alkoxy, an acyloxy, an amino, an alkylamino, a halogen, an alkyl, or a haloalkyl; $R_6$ is a hydrogen, an alkyl, or a haloalkyl; $A_1$ and $A_2$ is the same or different, each is direct link or alkylene; $X_1$ is a halogen, an oxygen, a sulfur, a sulphinyl, a sulphonyl, an amino, an alkylimino, or an alkylene; and $R_7$ is a hydrogen, a halogen, an alkoxy, a haloalkoxy, an acyloxy, a haloacyloxy, an aryloxy, a thioalkyl, a thioraryl, a sulphinyl, a haloalkyl sulphinyl, a sulphonyl, a haloalkylsulphonyl, an amino, an alkylimino, an acylamido group, a diacylamido group, a alkylacylamido group, a haloacylamido group, a haloalkylamino group, an isothiocyanate, an azide, a diazocarbonyl, a substituted oxirane, a β-chloroethylamine, or a phenyl optionally substituted with a halogen, a nitro group, an alkyl, a haloalkyl, a cyano, a hydroxyl, a carboxylic group, an amino, an alkylamino group, a dialkylamino group, a bisalkylamino group, a haloalkylamino group, a dihaloalkylamino group, a bishaloalkylamino group, an acylamido group, a diacylamido group, an alkylacylamido group, a haloacylamido group, a bis(haloacyl)imido group, an alkylhaloacylamido group, an isothiocyanate, an azide, a diazocarbonyl, a substituted oxirane, a β-chloroethylamine, or with a reactive derivative of said acid.

A suitable reactive derivative of an acid is, for example, an acid anhydride, or an acyl halide, for example an acyl chloride, or a lower allyl ester of said acid, for example the methyl or ethyl ester. Preferably the reaction is carried out in N,N-dimethylacetamide solution using an acyl chloride (prepared from the acid and thionyl chloride) as reactant.

A second preferred process for the manufacture of an acylanilide of the invention, wherein $R_5$ is hydroxy and $X_1$ is sulphur or alkylimino, comprises the reaction of an epoxide of the formula:

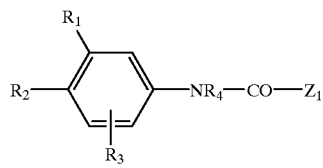

wherein $R_1$, $R_2$, $R_3$, and $R_4$ have the meanings stated above and wherein $Z_1$ has the formula:

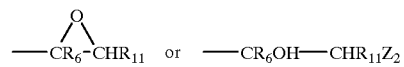

wherein $R_6$ has the meaning stated above, wherein $Z_2$ is a displaceable group and wherein $R_{11}$ is such that —$CHR_{11}$ is $A_1$ as stated above, with a thiol or amine of the formula:

wherein $R_7$ and $A_2$ have the meanings stated above and $R_{10}$ is an alkyl.

A suitable value for $Z_2$ is, for example, a halogeno or sulphonyloxy group, for example the chloro, bromo, iodo, methanesulphonyloxy, or p-toluenesulphonyloxy group. The above-mentioned reaction is preferably carried out in an inert diluent or solvent, for example tetrahydrofuran, and in the presence of a base, for example sodium hydride.

The epoxide used as starting material may be obtained by the epoxidation, for example with a base, of the corresponding haloanilide.

A third preferred process for the manufacture of an acylanilide of the invention, wherein $R_5$ is hydroxy, comprises the reaction of a compound of the formula:

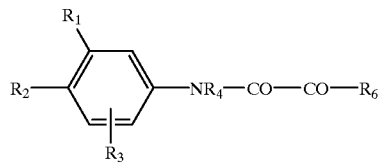

wherein $R_1$, $R_2$, $R_3$, $R_4$, and $R_6$ have the meanings stated above, with an organometallic compound of the formula:

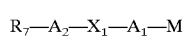

wherein $A_1$, $A_2$, $R_7$, and $X_1$ have the meanings stated above and M is a metal radical, for example the lithium radical.

The last-mentioned reaction is preferably carried out in an inert solvent, for example diethyl ether or tetrahydrofuran, at a low temperature, for example at between −60° C. and −100° C.

An acylanilide of the invention wherein $R_4$ and $R_5$ are joined together to form a carbonyloxy group, that is, an oxazolidinedione, may be prepared by the reaction of an isocyanate of the formula:

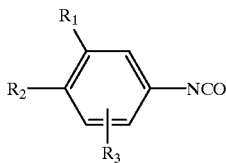

wherein $R_1$, $R_2$, and $R_3$ have the meanings stated above, with an ester of the formula:

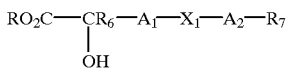

wherein $R_6$, $R_7$, $X_1$, $A_1$ and $A_2$ have the meanings stated above, and wherein R is alkyl of up to 6 carbon atoms, for example methyl or ethyl. This reaction is preferably carried out in an organic solvent, for example diethyl ether, at laboratory temperature.

An acylanilide of the invention wherein $R_5$ is hydroxy may be prepared by the hydrolysis of the corresponding acylanilide wherein $R_5$ is acyloxy, and an acylanilide of the invention wherein $R_5$ is hydroxy and $R_4$ is hydrogen may be prepared by the hydrolysis of the corresponding oxazolidinedione, which may be prepared as described in the preceding paragraph.

An acylanilide of the invention wherein $R_4$ is alkyl may be prepared by the alkylation of the corresponding acylanilide wherein $R_4$ is hydrogen.

An acylanilide of the invention wherein $R_5$ is acyloxy may be prepared by the acylation of the corresponding acylanilide wherein $R_5$ is hydroxy.

An oxazolidinedione of the invention, wherein $R_4$ and $R_5$ are joined together to form a carbonyloxy group, may be prepared by the reaction of the corresponding acylanilide wherein $R_4$ is hydrogen and $R_5$ is hydroxy with phosgene (COCl$_2$).

An acylanilide of the invention wherein $X_1$ or $X_2$ is sulphinyl or sulphonyl or wherein one or more of $R_1$, $R_2$, and a substituent in the phenyl or heterocyclic group $R_7$ is alkylsulphinyl, perfluoroalkylsulphinyl or phenylsulphinyl, or is alkylsulphonyl, perfluoroalkylsulphonyl or phenylsulphonyl, may be prepared by the oxidation of the corresponding acylanilide wherein $X_1$ or $X_2$ is sulphur or wherein one or more of $R_1$, $R_2$ and a substituent in the phenyl or heterocyclic group $R_7$, is alkylthio, perfluoroalkylthio or phenylthio. The oxidizing agent and conditions used will determine whether a sulphinyl or a sulphonyl compound is obtained. Thus, oxidation with sodium metaperiodate in methanol solution at or below laboratory temperature will generally convert a thiocompound into the corresponding sulphinyl compound; and oxidation with a per-acid, for example m-chloroperbenzoic acid, in methylene chloride solution at or above laboratory temperature will generally convert a thio compound into the corresponding sulphonyl compound.

A fourth preferred process for the manufacture of compounds of the present invention begins with a reaction intermediate having the following formula:

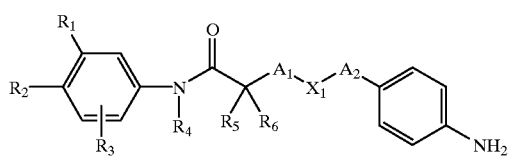

where $R_1$, $R_2$, $R_3$, $R_4$, $R_5$, $R_6$, $A_1$, $A_2$, and $X_1$ have the same meanings as stated above. $R_7$ is a substituted phenyl group having an amine group at the para- position. The reaction intermediate is reacted with any compound suitable for achieving N-acylation of the amine group. For example, an acyl halide or a haloacyl halide may be used to substitute an acyl group or haloacyl group at $R_8$ or $R_9$ to produce the compound below:

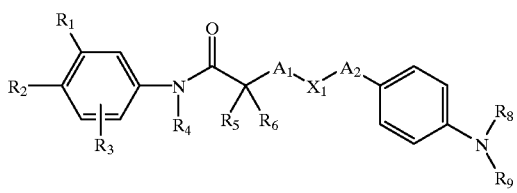

where $R_1$, $R_2$, $R_3$, $R_4$, $R_5$, $R_6$, $A_1$, $A_2$, and $X_1$ have the same meanings as stated above, and $R_8$ and $R_9$ are hydrogen, an alcyl group, or a haloacyl group. If desired, the resulting compounds may also be reacted with any compound suitable for achieving sulfonation of the sulfur at $X_1$, such as peracetic acid.

Another preferred process for the manufacture of compounds of the present invention is shown below.

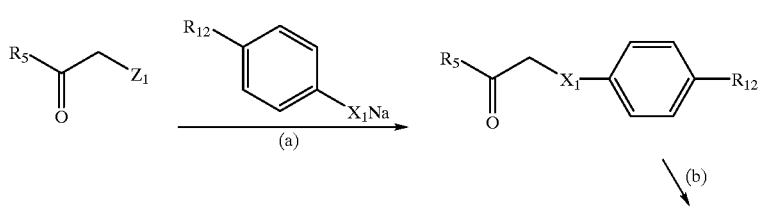

-continued

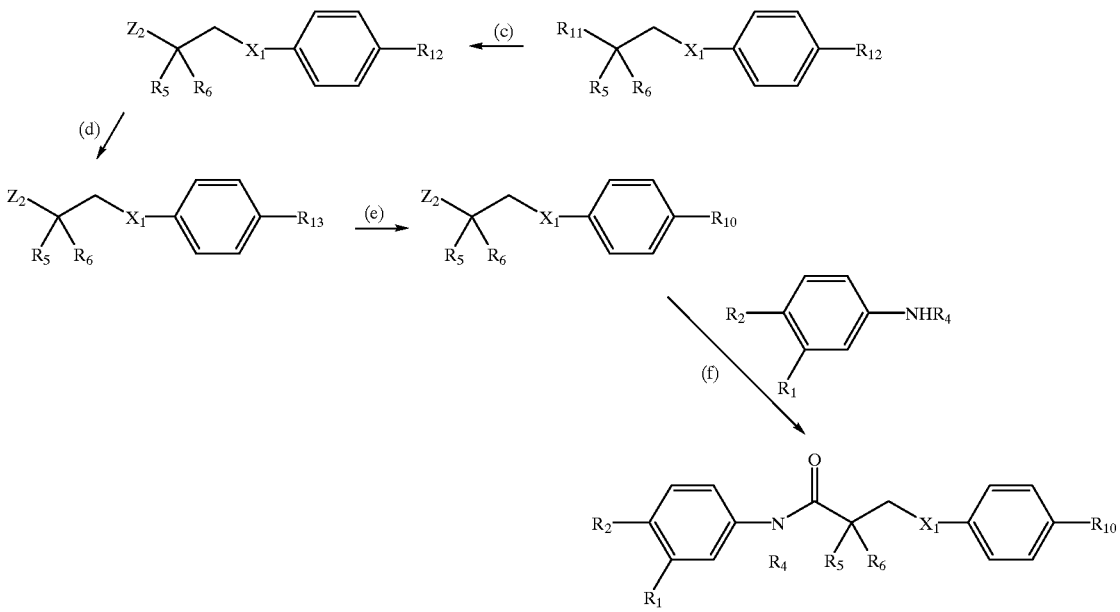

where $R_1$, $R_2$, $R_3$, $R_4$, $R_5$, $R_6$, $A_1$, $A_2$, and $X_1$, have the meanings as stated above and $R_7$ is a phenyl substituted with the substituents as described above. $Z_1$ is any suitable leaving group, preferably a halide or a methyl sulfide. $Z_2$ is any suitable acid, preferably a carboxylic acid. $R_{10}$ is an alkylacylamido. $R_{11}$ is any group which can be converted to an acid, such as a cyano group. $R_{12}$ is any group which can be converted to an amine, preferably a nitro group. $R_{13}$ is an amine or a substituted amine. The reactions occur under conditions effective to produce the desired compounds.

Depending upon the reaction scheme used to produce the non-steroidal agonist compounds of the present invention, it is possible to produce optically pure isomers. Otherwise, it is desireable to separate R- and S- enantiomers. A racemic acylanilide of the invention wherein $R_5$ is hydroxy may be separated into its optical isomers by forming an ester of the hydroxy group $R_5$ with an optically-active acid, for example (—)-camphanic acid, separating the diastereoisomeric esters thus obtained, by fractional crystallization or, preferably, by flash-chromatography, and then hydrolyzing each separate ester to the alcohol. Alternatively, an optically active acylanilide of the invention may be obtained by using any of the processes described above with an optically active starting material. The resulting enantiomer is substantially pure.

EXAMPLES

The following examples are provided to illustrate embodiments of the present invention but are by no means intended to limit its scope.
Example 1
 Equilibrium Disassociation Constant and Agonist Activity of Compounds
Materials and Methods
 Chemicals
 (17α-methyl-³H)-Mibolerone (³H-MIB, 83.5 Ci/mmol) and unlabeled MIB were purchased from DuPont Research NEN Products (Boston, Mass.). Triamcinolone acetonide, phenylmethylsulfonyl fluoride ("PMSF"), TRIS base, sodium molybdate and dithiothreitol were purchased from Sigma Chemical Company (St. Louis, Mo.). Hydroxyapatite ("HAP") was purchased from BIO-RAD Laboratories (Hercules, Calif.). EcoLite Plus™ scintillation cocktail was purchased from ICN Research Products Division (Costa Mesa, Calif.). Dulbecco's modified essential medium ("DMEM") and Lipofectamine™ transfection reagent were purchased from Life Technologies (Gaithersburg, Md.). Fetal bovine serum ("FBS") was purchased from Atlanta Biologicals, Inc. (Norcross, Ga.). All materials were used as received from the manufacturer.
Organic Synthesis
 R- and S-isomers of compounds C-1 to C-5 were prepared according to the general synthetic scheme reported for the enantiomers of bicalutamide using commercially available R-proline (Lancaster Synthesis, Wyndham, N.H.) as the chiral auxiliary (Mukheijee, et al., *Xenobiotica* 26:117-22 (1996); Tucker et al., *J. Med. Chem.* 31:885-87 (1988), which are hereby incorporated by reference). S-isomers were prepared using S-proline as chiral auxiliary. The structures of synthesized compounds were in accordance with the elemental analyses and spectroscopic data (¹H and ¹³C NMR, and IR).
 R-isomers of compounds C-6 to C-11 were prepared by N-acylation of an intermediate compound having the structure:

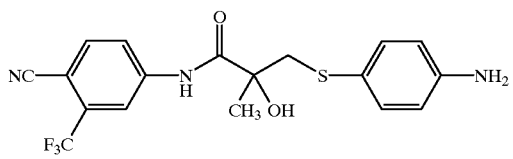

For compounds C-6 and C-7, sulfonation of the sulfur was achieved by treatment with peracetic acid in ethyl acetate at room temperature.
Preparation of Cytosolic Androgen Receptor
 Male Sprague-Dawley rats (Harlan Biosciences, Indianapolis, Ind.), weighing approximately 250 g, were castrated 24 hours prior to the removal of prostates. Ventral prostates were surgically removed, weighed, and immersed immediately in an ice-cold homogenization buffer consisting of 10 mM TRIS, 1.5 mM disodium EDTA, 0.5 mM dithiothreitol, 0.25 M sucrose, 10 mM sodium molybdate, and 1 mM PMSF adjusted to pH 7.2. The prostate tissue (about 0.4 g per rat) was minced, weighed, and homogenized (Model PRO 200 homogenizer, PRO Scientific, Monroe, Conn.) with 1 $\mu$L of the homogenization buffer per 500 mg of prostate tissue. The homogenate was then centrifuged at 114,000 g for 1 hour at 0° C. in an ultracentrifuge (Model L8-M, Beckman Instruments Inc., Palo Alto, Calif.). The supernatant (cytosol) containing AR protein was removed and stored at −80° C. until use.

Competitive Binding Studies

AR binding affinities of the synthesized ligands were determined by competitive binding in the presence of the high affinity AR ligand, $^3$H-mibolerone ("$^3$H-MIB"). In preliminary experiments, the equilibrium dissociation constant (Kd) of MIB was determined at 4° C. for 18 hours by incubating increasing concentrations of $^3$H-MIB (0.01 to 10 nM) with cytosol. The minimum concentration of $^3$H-MIB to saturate AR sites in the cytosol preparation was 1 nM. AR binding studies for the ligands of interest were then performed under identical conditions by incubating increasing concentrations ($10^{-3}$ nM to 10,000 nM) of each ligand with cytosol and a saturating concentration of $^3$H-MIB (1 nM). The incubate also contained 1 $\mu$M triamcinolone to prevent interaction of $^3$H-MIB with glucocorticoid and progesterone receptors (Carlson and Katzenellenbogen, *J. Steroid Biochem.* 36:549-61 (1990), which is hereby incorporated by reference). For the determination of non-specific binding, separate experiments were conducted by adding 1,000 nM MIB to the incubate. Unless otherwise indicated, all experiments were repeated three times or more. Separation of bound and free radioactivity at the end of incubation was achieved by the HAP method, as previously described (Mukheijee, et al., *Xenobiotica* 26:117-22 (1996), which is hereby incorporated by reference), and 0.8 mL of the ethanolic supernatant was added to 5 mL of scintillation cocktail. Radioactivity was counted in a liquid scintillation counter (Model LS6800, Beckman Instruments Inc., Palo Alto, Calif.).

Data Analysis of AR Binding Affinity

To determine the Kd of MIB, data were analyzed using a modified form of the Scatchard equation:

$$B/F = -(B/K_d) + B_{max}/K_d \qquad \text{(Equation 1)}$$

where B was the concentration of specifically-bound $^3$H-MIB in the incubate, F was the concentration of free $^3$H-MIB in the incubate, and $B_{max}$ was the maximum concentration of $^3$H-MIB specifically bound to AR, which is also the concentration of available AR binding sites in the incubate. Experimental data were computer-fit to equations using fortran subroutines written for PCNONLIN (SCI Software, Lexington, Ky.).

For competition binding experiments, competitive displacement curves were constructed for each ligand with percent specific binding (specific binding of $^3$H-MIB at a particular ligand concentration expressed as a percentage of the specific binding of $^3$H-MIB in the absence of ligand) on the vertical axis and ligand concentration on the horizontal axis. The ligand concentration that reduced the percentage of specific binding by 50% ($IC_{50}$) was determined by computer-fitting the data for each ligand to the following equation:

$$B = B_0\{1-(C/IC_{50}+C)\} \qquad \text{(Equation 2)}$$

where $B_0$ is the specific binding of $^3$H-MIB in the absence of ligand, and C is the ligand concentration. Binding affinities of the ligands were then compared using the equilibrium dissociation constant (Ki) of each ligand, as calculated using the equation below:

$$Ki=\{(IC_{50}*Kd)/(L+Kd)\} \qquad \text{(Equation 3)}$$

where Kd was the equilibrium dissociation constant of $^3$H-MIB as determined in Equation 1, and L was the concentration of $^3$H-MIB in the incubate (i.e., 1 nM). Low Ki values are associated with agonist activity. The relative binding affinity ("RBA") of each compound was calculated according to the equation below:

$$RBA=\{(IC_{50}\text{ of }DHT)/(IC_{50}\text{ of a ligand})\}*100\% \qquad \text{(Equation 4)}$$

Transcriptional Activation

The agonist activity of each ligand was examined using transfected CV-1 cells (American Type Culture Collection, Rockville, Md.). CV-1 cells were maintained in DMEM containing 10% FBS at 37° C. in a humidified atmosphere containing 5% carbon dioxide. DMEM without phenol red was used during transfection studies. One day before transfection, monolayer cells were removed from flasks and plated at a density of 4.5×10$^5$ cells/well in 6-well tissue culture plates. Cells in each well were then cotransfected with 100 ng of an AR expression vector (plasmid pCM-VhAR; provided by Dr. Elizabeth Wilson at The University of North Carolina, Chapel Hill, N.C.), 2.5 $\mu$g of a luciferase reporter vector (plasmid pMMTV-Luc; provided by Dr. Ronald Evans at The Salk Institute, San Diego, Calif.), and 2.5 $\mu$g of a control $\beta$-galactosidase vector (plasmid pSV-$\beta$-galactosidase; Promega Corporation, Madison, Wis.). Transfection was performed using Lipofectamine™ according to the manufacturer's instructions (Life Technologies, Gaithersburg, Md.). Ten hours after adding the transfection reagent, cells were washed twice with DMEM containing 0.2% FBS and then returned to the incubator. After an additional 10 to 12 hours of incubation, the medium was removed and replaced with DMEM containing 0.2% FBS and various concentrations of DHT or the ligand of interest. Final ligand concentrations were 0.1, 1, 10, 50, 100, 500, and 1,000 nM. The drug-containing medium was replaced after 24 hours of incubation to minimize the possible effects of ligand degradation on measurement of transcriptional activation. Control studies in which neither DHT nor ligand were added to the medium were also performed. Cells were washed with phosphate buffered saline, pH 7.4, after 48 hours of drug treatment and harvested using 350 $\mu$L of reporter lysis buffer (Promega Corporation, Madison, Wis.). Cell lysates were transferred to a microcentrifuge tube, vortexed briefly, and centrifuged at 12,000 g for 2 minutes; An aliquot (150 $\mu$L) of supernatant was used for determination of $\beta$-galactosidase activity in each well using a spectrophotometer (Cary Model 1E, Varian Associates, Sunnyvale, Calif.) set at a wavelength of 420 nm. A separate aliquot (100 $\mu$L) was used for determination of luciferase activity assay (Luciferase Assay System, Promega Corporation, Madison, Wis.) using an automated luminometer (Model AutoLumat LB953, Wallac Inc., Gaithersburg, Md.). Viable cell numbers and transfection efficiency in each well were normalized by expressing the transcriptional activation as a ratio of the luciferase activity to $\beta$-galactosidase activity in individual wells. The efficacy of individual compounds compared to DHT was then calculated by dividing (the maximal transcriptional activation observed for each ligand) by (the maximal transcriptional activation observed for DHT). All experiments were performed in triplicate. Potency was reported as the lowest concentration of the ligand used during transfection experiments capable of producing maximal AR-mediated transcriptional activation.

Results

The values for the equilibrium disassociation constant (Ki) and agonist activity of the R-isomers of compounds C-1 through C-5 are shown in Table 1 below.

TABLE 1

| Ligand | Ki (nM) | Agonist Activity[a] (% of DHT) | Potency[b] (nM) |
|---|---|---|---|
| DHT | 0.28 ± 0.02 | 100[d] | 1 nM |
| R-Bicalutamide | 11.0 ± 1.5[c] | 8.28 ± 2.66 | 1,000 nM |
| C-1 | 1.65 ± 0.10 | 97.5 ± 21.6 | 100 nM |
| C-2 | 7.98 ± 0.86 | 18.5 ± 5.08 | 500 nM |
| C-3 | 0.30 ± 0.12 | 82.9 ± 14.0 | 500 nM |
| C-4 | 2.79 ± 1.35 | 20.5 ± 7.57 | 500 nM |
| C-5 | 0.86 ± 0.11 | 88.6 ± 18.0 | 500 nM |

[a]Maximal percentage of transcriptional activation observed for each ligand.
[b]The lowest concentration of the ligand capable of maximally stimulating AR-mediated transcription during transfection experiments.
[c]Mukherjee, et al., Xenobiotica 26:117-22 (1996).
[d]Ratio of luciferase activity to β-galactosidase activity was 397 ± 144 in the absence of any ligand (control) and 145,000 ± 33,000 in the presence of 1 nM DHT.

The Kd for $^3$H-MIB (0.19±0.01 nM; mean±S.D., n=3) and the binding affinity of DHT (Table 1) were similar to previously reported values (Mukherjee, et al., *Xenobiotica* 26:117-22 (1996); Wilson and French, *J. Biol. Chem.* 251:5620-29 (1976), both of which are hereby incorporated by reference). The Ki of R-bicalutamide was also similar to that previously reported, and was consistent with the binding affinity of other known nonsteroidal antiandrogens (Teutsch, et al., *J. Steroid Biochem. Molec. Biol.* 48:111-19 (1994); Mukherjee, et al., *Xenobiotica* 26:117-22 (1996); Tucker and Chesterson, *J. Med. Chem.* 31:885-87 (1988), all of which are hereby incorporated by reference).

Surprisingly, several R-isomers of these analogs bound the AR with affinity similar to that of DHT, and with much greater affinity than R-bicalutamide (Table 1). Substitution with a chloroacetamido (C-1) group at the para-position of the aromatic ring resulted in a significant increase in AR binding affinity. Likewise, ligands lacking the sulfonyl moiety and a second aromatic ring (C-2 to C-5) bound the AR with high affinity. Further, it is important to note that this affinity could be increased by replacing the para-cyano moiety with a nitro- functional group, suggesting that hydrogen bonding at this position may be critical to interaction with the AR. Further structural modifications to introduce the para-nitro substituent in ligands maintaining both aromatic rings (e.g. C-1) may therefore prove useful in identifying additional lead compounds. The equilibrium disassociation constant (Ki value) of the S-isomers of compounds C-1 through C-5 was at least 10-fold greater than the Ki values for R-isomers in all cases. Thus, only the R-isomers of the synthesized analogs were evaluated for their ability to stimulate AR-mediated transcriptional activation.

In all cases, AR-mediated transcriptional activation increased with increasing ligand concentrations and then plateaued at higher concentrations. However, the agonist activity (i.e., maximal degree of AR-mediated transcriptional activation observed) and potency (i.e., the lowest concentration of ligand capable of inducing maximal transcriptional activation) differed greatly between ligands (Table 1). For example, R-bicalutamide, a known antiandrogen, was unable to stimulate AR-mediated transcriptional activation at even the highest concentrations tested (i.e., mean agonist activity of 8.3% at 1,000 nM). Similarly, compounds C-2 and C-4 which lack the sulfonyl moiety and second aromatic ring produced only minimal (<20%) agonist activity. As noted in our studies of AR binding affinity, substitution of a para-nitro functional group significantly increased the degree of agonist activity elicited by this series of ligands (e.g. compare C-2 to C-3 and C-4 to C-5). However, the potency of these compounds was approximately 500-fold lower than that observed with DHT. Structural modifications to include the chloroacetamido-functional group at the para-position (ligand C-1) resulted in the most potent agonist activity. Ligand C-1 demonstrated a mean efficacy of approximately 98% at concentrations as low as 100 nM. Despite the electrophilic character of the chloroacetamido- substituent, studies have shown that this ligand does not covalently (i.e., irreversibly) bind the AR. Another modification to the second aromatic ring includes a ligand incorporating an mono- or di-acetamido-functional group at the para- position.

Example 2

Binding Affinity of Compounds

Due to the relative binding affinity and equilibrium dissociation constants (Ki) for compound C-1, additional analysis was provided for the compounds listed in the Table 2 below. Ki and RBA were calculated as described above.

TABLE 2

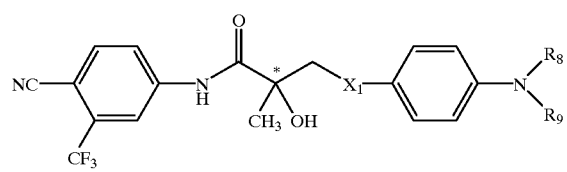

| Compound No. | Isomer | $X_1$ | $R_8$ | $R_9$ | RBA (%) | Ki (nM) |
|---|---|---|---|---|---|---|
| C-6 | (R) | $SO_2$ | $COCH_2Cl$ | H | 0.66 | 40.9 |
| C-7 | (R) | $SO_2$ | $COCH_3$ | H | 15.9 | 1.70 |
| C-8 | (R) | S | $COCH_3$ | H | 26.9 | 1.00 |
| C-9 | (R) | S | $COCH_3$ | $COCH_3$ | 10.2 | 2.64 |
| C-10 | (R) | S | $COCH_2Me$ | H | 7.08 | 3.81 |
| C-11 | (R) | S | $COCH_2Me$ | $COCH_2Me$ | <0.10 | >1000 |

TABLE 2-continued

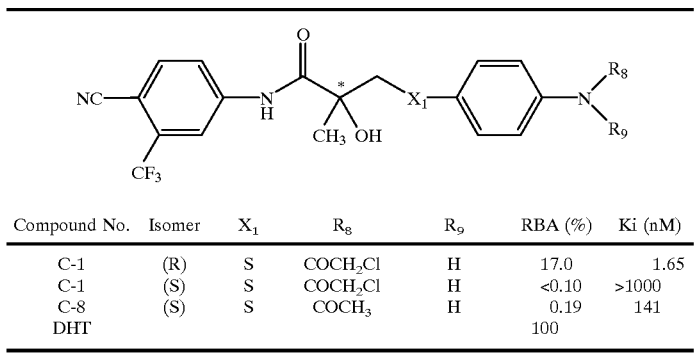

| Compound No. | Isomer | $X_1$ | $R_8$ | $R_9$ | RBA (%) | Ki (nM) |
|---|---|---|---|---|---|---|
| C-1 | (R) | S | $COCH_2Cl$ | H | 17.0 | 1.65 |
| C-1 | (S) | S | $COCH_2Cl$ | H | <0.10 | >1000 |
| C-8 | (S) | S | $COCH_3$ | H | 0.19 | 141 |
| DHT | | | | | 100 | |

Example 3
Synthesis of Compounds (R)- and (S)-enantiomers of compounds of the present invention were synthesized by mono- or diacylation of the reaction intermediate, as well as sulfonation thereof. More specifically, non-steroidal agonist compounds C-1, C-6, C-10, and C-11 are prepared according to the schemes below.

compound C-1. In step (b), compound C-1 is treated with peracetic acid in ethyl acetate at room temperature to form compound C-6. In step (c), the intermediate compound is treated with propanoyl bromide (EtCOBr) in $CH_2Cl_2$ at room temperature to form compounds C-10 and C-11, which are separated from one another by column separation.

In addition, non-steroidal agonist compounds C-7, C-8, and C-9 were prepared according to the schemes below.

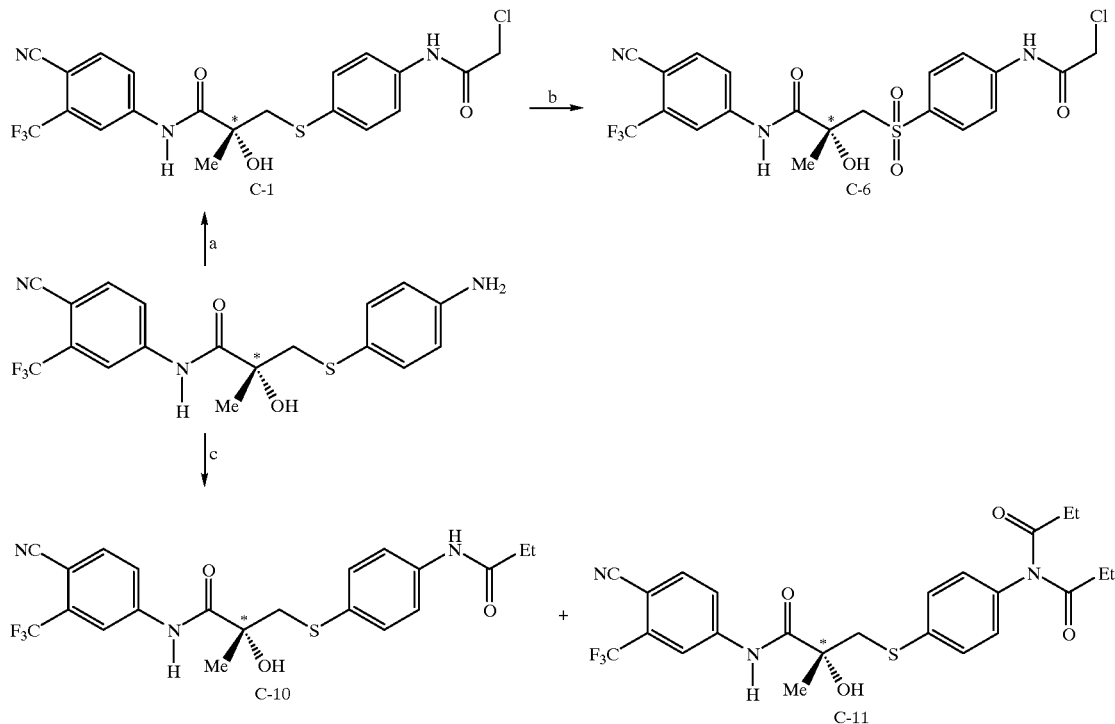

In step (a), the intermediate compound is reacted with $ClCH_2COCl$ in $CH_2Cl_2$ at room temperature to produce

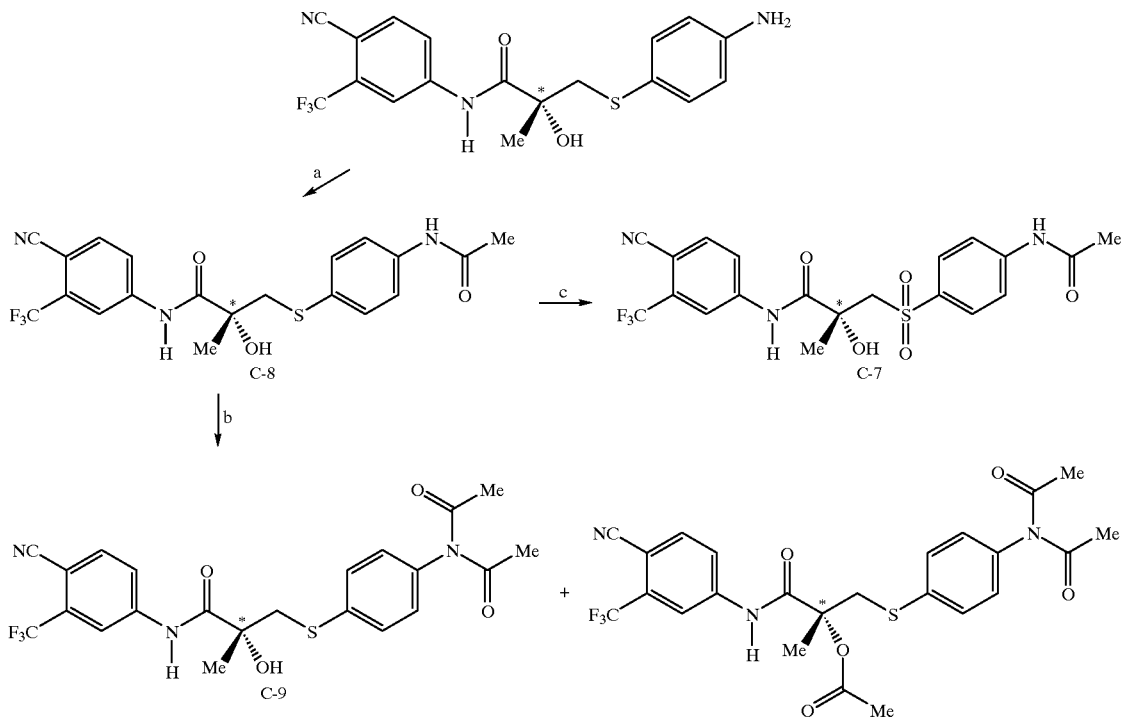

In step (a), the intermediate compound is treated with acid anhydride at room temperature to form compound C-8. In step (b), compound C-8 is treated with acid anhydride to form compound C-9, which is separated from the by-product compound by reflux and column separation. In step (c), compound C-8 is treated with peracetic acid in ethyl acetate at room temperature to yield compound C-7.

Non-steroidal agonist compounds C-12, C-13, C-14, and C-15 were prepared according to the scheme below.

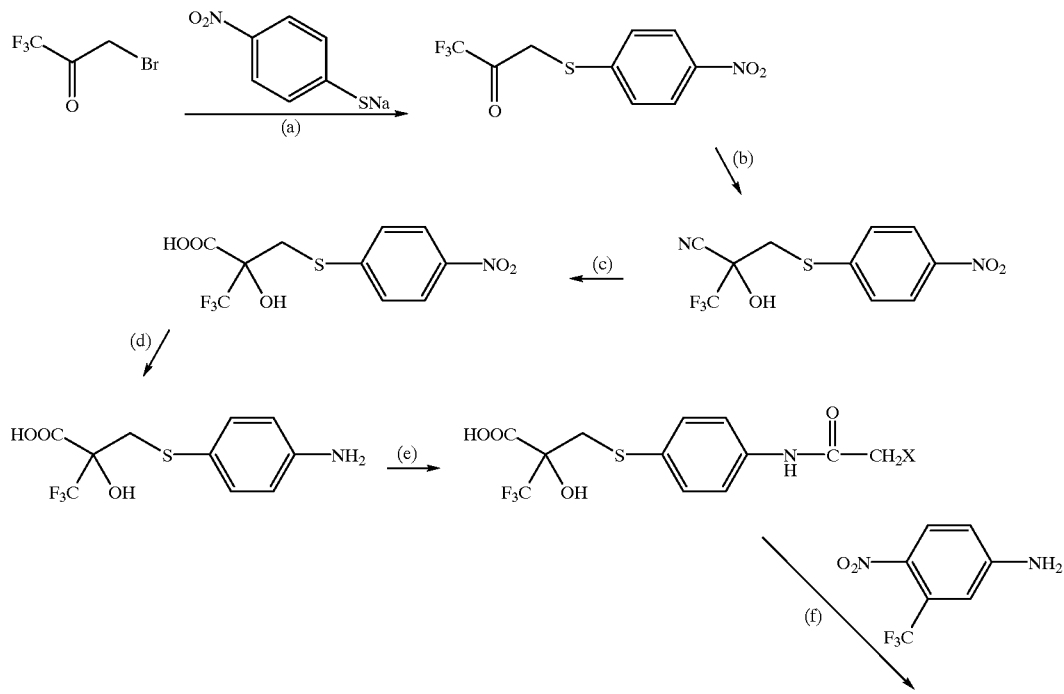

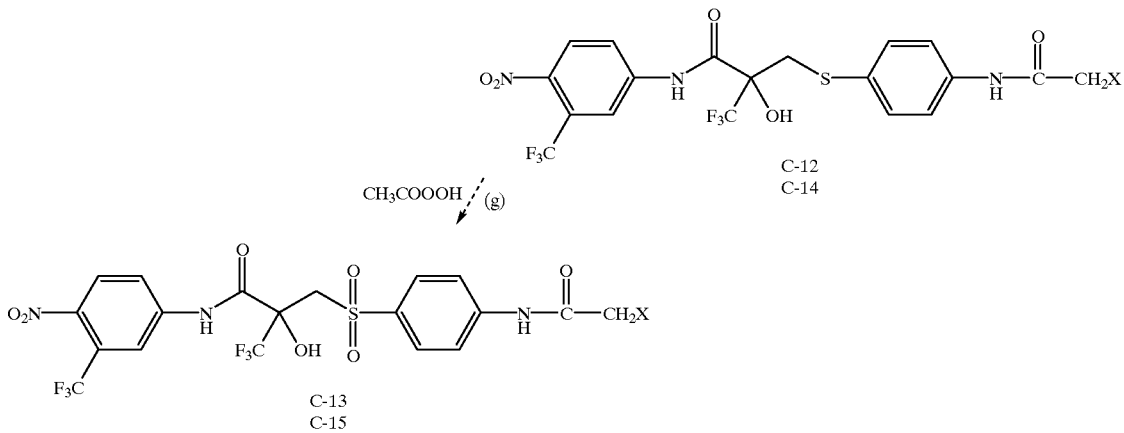

In step (a), a solution of 4.6 g (26 mmol.) sodium salt of p-nitrothiophenol (prepared according to the procedure of Holt et al. (J. Am. Chem. Soc. 46:2331 (1924), which is hereby incorporated by reference) in 30 mL anhydrous tetrahydrofuran ("THF") was cooled to 5° C. and 5 g (26 mmol. ) 3-bromo-1,1,1-trifluoroacetone was added dropwise. The reaction mixture was allowed to warm up to room temperature and was stirred for 3 hours. The reaction mixture was then filtered and the precipitate washed with THF. The filtrate and washings were combined and evaporated. The residue was separated on a column with Silicagel (eluent chloroform - methanol 15:1). Fractions with 3-(4-nitro-phenylthio)-1,1,1-trifluoropropan-2-one were combined and evaporated.

In step (b), the yield from step (a) was added to a cooled solution of 1 g (15 mmol.) potassium cyanide in water (5 mL) at a rate that maintained temperature of the reaction mixture below 5° C. The mixture was cooled to 0° C. and 3.4 mL 25% sulfuric acid was added dropwise while the temperature was kept below 5° C. The reaction mixture was warmed to room temperature and stirred for 20 hours. The reaction mixture was diluted with water (50 mL) and extracted with ether (3×150 mL). Combined ether extracts were washed with saturated sodium bicarbonate solution, brine, and dried over sodium sulfate. Solvent was evaporated and 3-(4-nitro-phenylthio)-1,1,1-trifluoropropan-2-one cyanohydrin was obtained as an yellow oil, which solidified in high vacuum.

In step (c), the yield from step (b) was mixed with 20 mL of a concentrated hydrochloric acid - glacial acetic acid (6:1) mixture. The mixture was heated to reflux with vigorous stirring for 20 hours, then cooled to room temperature, diluted with water (100 mL), and extracted with ether (4×100 mL). Ether extracts were combined and washed with saturated sodium bicarbonate solution. The aqueous phase was acidified with hydrochloric acid to pH 1 and extracted with ether (4×150 mL). Ether extracts were combined, dried over $MgSO_4$, filtered, evaporated, and dried in high vacuum. The resulting oil crystallized after stirring with ligroin. The product, 2-hydroxy-2-(trifluoromethyl)-3-(3-nitro-phenylthio)propionic acid, was filtered and dried in high vacuum.

In step (d), 1.36 g (6 mmol) tin (II) chloride dihydrate was dissolved in 2 mL concentrated hydrochloric acid and cooled to 5° C. 0.6 g (2 mmol.) of the yield from step (c) was dissolved in methanol (2 mL) and added dropwise to the reaction flask. The reaction mixture was stirred at room temperature for 24 hours. The reaction mixture was evaporated and used for the next reaction as an oil without further purification.

In step (e), the yield from step (d) was dissolved in 25 mL anhydrous acetonitrile and transferred to a reaction flask containing 1 g anhydrous calcium carbonate. 0.1 mL (1.2 mmol.) chloroacetylchloride or acetyl chloride (X=H or Cl) was added slowly and the reaction mixture stirred for 48 hours. The reaction mixture was evaporated and separated by column chromatography (Silicagel, methylene chloride-ethyl acetate 95:5).

In step (f), the yield from step (e) was dissolved in 9 mL anhydrous dimethylacetamide and cooled to −15° C. 0.1 mL (1.5 mmol.) thionyl chloride was added slowly at a rate that maintained the temperature of the reaction mixture below −10° C. The reaction mixture was stirred for 1 hour and the solution of 206 mg (1 mmol.) of 5-amino-2-nitrobenzotrifluoride in 3 mL anhydrous DMA was added dropwise while keeping temperature below −10° C. The reaction mixture was allowed to warm up to room temperature and then stirred 72 hours, evaporated, diluted with saturated sodium bicarbonate solution, extracted with ether, evaporated, and separated by column chromatography (Silicagel, chlorophorm-methanol 19:1). Compound C-12 or C-14 was recovered from the column.

Optionally, at step (g), compounds C-12 or C-14 were oxidized by peracetic acid to form corresponding sulfo-derivatives C-13 or C-15, respectively.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. A method of suppressing spermatogenesis in a male patient comprising:

contacting an androgen receptor of a male patient with a non-steroidal agonist compound having a formula:

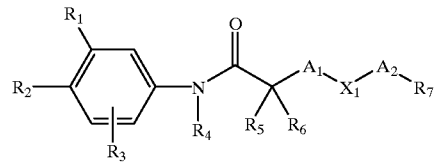

where $R_1$, $R_2$, and $R_3$ are the same or different and are a hydrogen, a nitro, a cyano, a carbamoyl, a halogen, a perfluoroalkyl, a haloalkylamido, an isothiocyanate, an azide, a diazocarbonyl, a substituted oxirane, or a β-chloroethylamine;

$R_4$ is a hydrogen, an alkyl, or is joined to $R_5$;

$R_5$ is a hydrogen, a hydroxy, an alkoxy, an acyloxy, an amino, an alkylamino, a halogen, an alkyl, a haloalkyl, or is joined to $R_4$;

$R_6$ is a hydrogen, an alkyl, or a haloalkyl;

$A_1$ and $A_2$ are the same or different, and each is a direct link or an alkylene;

$X_1$ is an oxygen, a sulfur, a sulphinyl, a sulphonyl, an amino, an alkylimino, or an alkylene, $R_7$ is a hydrogen, a halogen, an alkoxy, a haloalkoxy, an acyloxy, a haloacyloxy, an aryloxy, a thioalkyl, a thioraryl, an amino, an alkylimino, an alkylamido group, a haloalkylamido group, or a phenyl optionally substituted with a halogen, a nitro group, an alkyl, a haloalkyl, a cyano, a hydroxyl, a carboxylic group, an amino, an alkylamino group, a dialkylamino group, a bisalkylamino group, a haloalkylamino group, a dihaloalkylamino group, a bishaloalkylamino group, an acylamido group, a diacylamido group, an alkylacylamido group, a haloacylamido group, a bis(haloacyl)imido group, or an alkylhaloacylamido group.

2. A method according to claim 1, wherein $R_1$ is $CF_3$, $R_2$S CN or $NO_2$, $R_3$ and $R_4$ are H, $R_5$ is OH, $R_6$ is $CH_3$ or $CF_3$, $A_1$ is an alkylene or a direct link, $A_2$ is a direct link, $X_1$ is $CH_2$, S, or $SO_2$, and $R_7$ is Br, I, or a phenyl ring optionally substituted with a halogen, a nitro group, an alkyl, a haloalkyl, a cyano, a hydroxyl, a carboxylic group, an amino, an alkylamino group, a dialkylamino group, a bisalkylamino group, a haloalkylamino group, a dihaloalkylamino group, a bishaloalkylamino group, an acylamido group, a diacylamido group, an alkylacylamido group, a haloacylamido group, a bis(haloacyl)imido group, or an alkylhaloacylamido group.

3. A method according to claim 2, wherein $A_1$ is an alkylene, $X_1$ is S or $SO_2$, and $R_7$ has the formula:

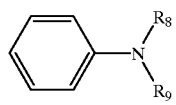

wherein $R_8$ is $COCH_3$, $COCH_2Cl$, or $COCH_2CH_3$, and $R_9$ is H, $COCH_3$, or $COCH_2CH_3$.

4. A method according to claim 1, wherein the non-steroidal agonist compound is a substantially pure R enantiomer.

5. A method of hormone therapy comprising:

contacting an androgen receptor of a male patient with a non-steroidal agonist compound under conditions effective to effect a change in an androgen-dependent condition, the non-steroidal agonist compound having a formula:

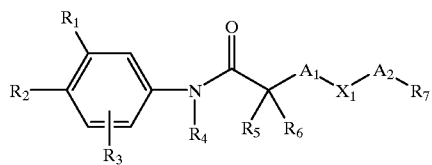

where $R_1$, $R_2$, and $R_3$ are the same or different and are a hydrogen, a nitro, a cyano, a carbamoyl, a halogen, a perfluoroalkyl, a haloalkylamido, an isothiocyanate, an azide, a diazocarbonyl, a substituted oxirane, or a β-chloroethylamine;

$R_4$ is a hydrogen, an alkyl, or is joined to $R_5$;

$R_5$ is a hydrogen, a hydroxy, an alkoxy, an acyloxy, an amino, an alkylamino, a halogen, an alkyl, a haloalkyl, or is joined to $R_4$;

$R_6$ is a hydrogen, an alkyl, or a haloalkyl;

$A_1$ and $A_2$ are the same or different, and each is a direct link or an alkylene;

$X_1$ is an oxygen, a sulfur, a sulphinyl, a sulphonyl, an amino, an alkylimino, or an alkylene;

$R_7$ is a hydrogen, a halogen, an alkoxy, a haloalkoxy, an acyloxy, a haloacyloxy, an aryloxy, a thioalkyl, a thioraryl, an amino, an alkylimino, an alkylamido group, a haloalkylamido group, or a phenyl optionally substituted with a halogen, a nitro group, an alkyl, a haloalkyl, a cyano, a hydroxyl, a carboxylic group, an amino, an alkylamino group, a dialkylamino group, a bisalkylamino group, a haloalkylamino group, a dihaloalkylamino group, a bishaloalkylamino group, an acylamido group, a diacylamido group, an alkylacylamido group, a haloacylamido group, a bis(haloacyl)imido group, or an alkylhaloacylamido group.

6. A method according to claim 5, wherein $R_1$ is $CF_3$, $R_2$ is CN or $NO_2$, $R_3$ and $R_4$ are H, $R_5$ is OH, $R_6$ is $CH_3$ or $CF_3$, $A_1$ is an alkylene or a direct link, $A_2$ is a direct link, $X_1$ is $CH_2$, S, or $SO_2$, and $R_7$ is Br, I, or a phenyl ring optionally substituted with a halogen, a nitro group, an alkyl, a haloalkyl, a cyano, a hydroxyl, a carboxylic group, an amino, an alkylamino group, a dialkylamino group, a bisalkylamino group, a haloalkylamino group, a dihaloalkylamino group, a bishaloalkylamino group, an acylamido group, a diacylamido group, an alkylacylamido group, a haloacylamido group, a bis(haloacyl)imido group, or an alkylhaloacylamido group.

7. A method according to claim 6, wherein $A_1$ is an alkylene, $X_1$ is S or $SO_2$, and R₇ has the formula:

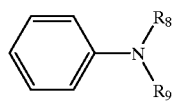

wherein $R_8$ is $COCH_3$, $COCH_2Cl$, or $COCH_2CH_3$, and $R_9$ is H, $COCH_3$, or $COCH_2CH_3$.

8. A method according to claim 5, wherein the non-steroidal agonist compound is a substantially pure R enantiomer.

9. A method according to claim 5, wherein the androgen-dependent condition is selected from a group consisting of hypogonadism, sarcopenia, crythropoicsis, and osteopoaosis.

* * * * *